US006416473B1

United States Patent
Risk et al.

(10) Patent No.: US 6,416,473 B1
(45) Date of Patent: Jul. 9, 2002

(54) METHODS AND APPARATUS FOR PROVIDING AN INDICATOR OF AUTONOMIC NERVOUS SYSTEM FUNCTION

(75) Inventors: Marcelo R. Risk, Melrose; Alan M. Cohen, Newton, both of MA (US); Daniel T. Kaplan, St. Paul, MN (US)

(73) Assignee: Boston Medical Technologies, Inc., Wakefield, MA (US)

( * ) Notice: Subject to any disclaimer, the term of this patent is extended or adjusted under 35 U.S.C. 154(b) by 0 days.

(21) Appl. No.: 09/592,955

(22) Filed: Jun. 13, 2000

(51) Int. Cl.[7] .................................................. A61B 5/00

(52) U.S. Cl. ...................... 600/300; 600/485; 600/301; 600/500; 600/509; 600/521

(58) Field of Search .................. 600/509, 513, 600/521, 483–485, 516, 300, 600, 301, 500

(56) References Cited

U.S. PATENT DOCUMENTS

| | | | | |
|---|---|---|---|---|
| 5,299,119 A | * | 3/1994 | Kraf et al. | 600/516 |
| 5,419,338 A | * | 5/1995 | Sarma et al. | 600/516 |
| 5,797,840 A | * | 8/1998 | Akselrod et al. | 600/300 |

OTHER PUBLICATIONS

C.R. Weinberg et al., "An Improved Method for Measuring Heart–Rate Variability: Assessment of Cardiac Autonomic Function", Biometrics, Biometric Society, 1984, vol. 40, No. 3, pp. 855–861.

D. Ziegler et al., "Assessment of Cardiovascular Autonomic Function: Age–related Normal Ranges and Reproducibility of Spectral Analysis, Vector Analysis, and Standard Tests of Heart Rate Variation and Blood Pressure Responses", Diabetic Medicine, 1992:9, pp. 166–175.

J. Philip Saul, "Beat–to–Beat Variations of Heart Rate Reflect Modulation of Cardiac Autonomic Outflow", NIPS, vol. 5, Feb. 1990, pp. 32–37.

A. Verrotti et al., "Autonomic Neuropathy in Diabetic Children", J. Paediatr. Child Health (1995) 31. Pp. 545–548.

"Consensus Statement Report and Recommendations of the San Antonio Conference on Diabetic Neuropathy", Diabetes, vol. 37, Jul. 1988, pp. 1000–1004.

Iain A. D. O'Brien et al., "Heart Rate Variability in Healthy Subjects: Effect of Age and the Derivation of Normal Ranges for Tests of Autonomic Function", Br Heart 1986; 55, pp. 348–354.

D. J. Ewing, "Cardiac Autonomic Neuropathy", Chapter 5 Jarrett (ed) Diabetes and Heart Disease, 1984, pp. 99–127.

Basil F. Clarke, M.D. et al., "Cardiovascular Reflex Tests", New York State Journal of Medicine, May 1984, pp. 903–908.

(List continued on next page.)

*Primary Examiner*—Robert L. Nasser
(74) *Attorney, Agent, or Firm*—Daly, Crowley & Mofford, LLP

(57) ABSTRACT

Methods and apparatus for providing a single, accurate indicator of a patient's autonomic nervous system function are described. The indicator is a combination of results of a plurality of different autonomic nervous system tests performed on the patient and referenced to a cross-sectional population. In one embodiment, the results of the different autonomic nervous system tests are referenced to a limited age group of the cross-sectional population. A method according to the invention includes generating a mathematical expression for each of the autonomic nervous system tests as a function of physiological data of the cross-sectional population, inserting measured physiological data of the patient into the mathematical expressions to compute output values for each of the tests, and combining the output values to provide the autonomic function indicator.

23 Claims, 13 Drawing Sheets

OTHER PUBLICATIONS

D. Ziegler et al., "The Epidemiology of Diabetic Neuropathy", 1992 Journal of Diabetes and Its Complications, 1 Diab. Comp: 6:1, pp. 49–57.

Consensus Development Conference Report, "Consensus Development Conference on the Diangnosis of Coronary Heart Disease in People with Diabetes", Diabetes Care, vol. 21, No. 9, Sep. 1998, pp. 1551–1559.

Aaron I. Vinik, M.D., et al., "Autonomic Neuropathy", Diabetic Complications, pp. 165–176.

Mary P. Schumer et al., "Cardiovascular Autonomic Neuropathy Testing in Patients with Diabetes", Diabetes Spectrum, vol. 11, No. 4, 1998, pp. 227–231.

* cited by examiner

METHODS AND APPARATUS FOR PROVIDING AN INDICATOR OF AUTONOMIC NERVOUS SYSTEM FUNCTION

CROSS-REFERENCE TO RELATED APPLICATIONS

Not applicable.

STATEMENT REGARDING FEDERALLY FUNDED RESEARCH

Not applicable.

BACKGROUND OF THE INVENTION

The autonomic nervous system, which includes the sympathetic and the parasympathetic systems, governs involuntary actions of cardiac muscle and certain tissues of the human body. Autonomic nervous system neuropathy, which is sometimes referred to as visceral neuropathy, affects the nerves that serve the heart and internal organs and produces changes in many processes and systems. Symptoms of autonomic neuropathy include numbness and pain in the hands, feet, or legs, digestive dysfunction, sexual dysfunction, and orthostatic hypotension, disordered bowel, bladder or abnormal papillary reflexes.

Autonomic neuropathy is most commonly linked to diabetes, however, several causes are possible, including alcoholism, sleep apnea, and coronary artery disease. Thus, evaluation of the autonomic nervous system function has wide applicability, from diagnosing and treating patients with diabetes to detecting patients at risk for sudden death due to cardiac arrest.

One technique for detecting autonomic neuropathy is to analyze the variability of a patient's heart rate. Various tests have been used to exercise the autonomic nervous system for this purpose, including the Valsalva test and the Expiration/Inspiration (E/I) test which is sometimes referred to as the metronomic deep breathing test. The Valsalva test requires that the patient forcibly exhale to a predetermined pressure, such as 40 mmHg, for a predetermined duration, such as 15 seconds, during which the heart rate is monitored. Conventionally, the heart rate is measured by measuring the interval between certain phenomena of the patient's ECG signal, such as the interval between peaks of the QRS complex, or the R-R interval. Thereafter, the patient rests for a predetermined duration. The result of the Valsalva test is a ratio of the highest heart rate (as indicated by the shortest R-R interval) during the breathing maneuver to the lowest heart rate (as indicated by the longest R-R interval) during a recovery period after the maneuver. In accordance with the E/I test, the patient is instructed to breathe deeply at a frequency of 6 cycles/minute, which has been shown to produce maximal heart rate variability in healthy individuals. The result of the E/I test is a ratio of the average of the heart rate peaks to the average of the heart rate troughs.

Several additional tests of heart rate variability are described in one or more of the following papers: (1) D. Ziegler, et al. entitled "Assessment of Cardiovascular Autonomic Function: Age-related Normal Ranges and Reproducibility of Spectral Analysis, Vector Analysis, and Standard Tests of Heart Rate Variation and Blood Pressure Responses." Diabetic Medicine, Vol. 9, pgs. 166–175, 1992; (2) I. O'brien et al. entitled "Heart Rate Variability in Healthy Subjects: Effect of Age and the Derivation of Normal Ranges for Test of Autonomic Function," Br Heart J, 1986, 55:348–54; (3) D. Ewing, entitled "Cardiac Autonomic Neuropathy," Chapter 5, Jarret (ed) Diabetes and heart Disease, 1984 Elesvier Science Publishers B.V.; and (4) B. Clarke, et al. entitled "Cardiovascular Reflex Tests," New York State Journal of Medicine, May 1982, pages 903–908. Further heart rate variability tests including high frequency area under the Power Spectrum Density (PSD), low frequency area under the PSD, and very low frequency area under the PSD are described by J. Saul in "Beat-to-Beat Variations of Heart Rate Reflect Modulation of Cardiac Autonomic Outflow," NIPS, Volume 5: 32–7, February 1990.

Typically, the physician is provided with the individual test results and standard data against which to assess the results. The accuracy of heart rate variability evaluation as a measure of autonomic nervous system function is dependent on many factors, including the precision with which the patient follows the prescribed breathing regimen which affects the intra-patient reproducibility of the tests, the inter-patient reproducibility of the tests, and the accuracy with which the R-R intervals of the ECG signal are detected. Many improvements to the accuracy of heart rate variability evaluation have been made. For example, a system for enhancing a patient's compliance with a predetermined breathing regimen is described in U.S. patent application Ser. No. 08/942,710 entitled "METHOD AND APPARATUS FOR ENHANCING PATIENT COMPLIANCE DURING INSPIRATION MEASUREMENTS." Further, methods and apparatus for enhancing the accuracy of detection of R-R intervals are described in U.S. Pat. No. 5,984,954 entitled "METHODS AND APPARATUS FOR R-WAVE DETECTION."

SUMMARY OF THE INVENTION

It is an object of the present invention to provide an accurate indicator of a patient's autonomic nervous system function.

Another object of the invention is to provide a single value measure of a patient's autonomic nervous system function.

These and other objects of the invention are achieved by combining the results of different autonomic nervous system tests, each referenced to a cross-sectional population, to provide a single autonomic function indicator. A method according to the invention includes the steps of generating a plurality of mathematical expressions, each associated with a different autonomic nervous system test and being a function of physiological data from the cross-sectional population. The method further includes measuring physiological data of the patient and inserting the measured physiological data into each of the mathematical expressions to provide an output value for each of the mathematical expressions. The output values of each of the mathematical expressions are combined to provide the indicator of the patient's autonomic nervous system function.

The above-described method and the resulting autonomic function indicator provide a highly accurate assessment of a patient's autonomic nervous system function for several reasons. First, since the autonomic function indicator of the present invention is a composite of a plurality of autonomic nervous system measurements, errors associated with the performance and evaluation of individual tests are minimized, thereby enhancing both intra-patient and inter-patient reproducibility. Also, there is greater contrast between the autonomic function indicator of healthy individuals and those with autonomic neuropathy, as compared to conventional autonomic nervous system test results, thereby facilitating accurate interpretation of the indicator. Further, the autonomic function indicator of the present invention is provided in a standard form suitable for standardized interpretation (e.g., a value between 0 and 1) regardless of the number of different tests which are performed and used to provide the indicator. The autonomic nervous system function indicator provides a convenient tool for long-term tracking of a patient's autonomic nervous system function, and the efficacy of intervention.

In an illustrative embodiment, each mathematical expression is generated by sorting physiological data of the cross-sectional population, ranking the sorted data, normalizing the ranked data, plotting the sorted data with respect to the normalized data, interpolating the plotted data, and representing the interpolated data as the mathematical expression. Preferably, the interpolation is a linear interpolation and the resulting mathematical expression is a line function.

In accordance with a further aspect of the invention, the mathematical expression generated for each autonomic nervous system test is a function of the age of the patient. With this arrangement, the natural degradation of the autonomic nervous system which occurs with age does not affect the indicator.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Figure 1:
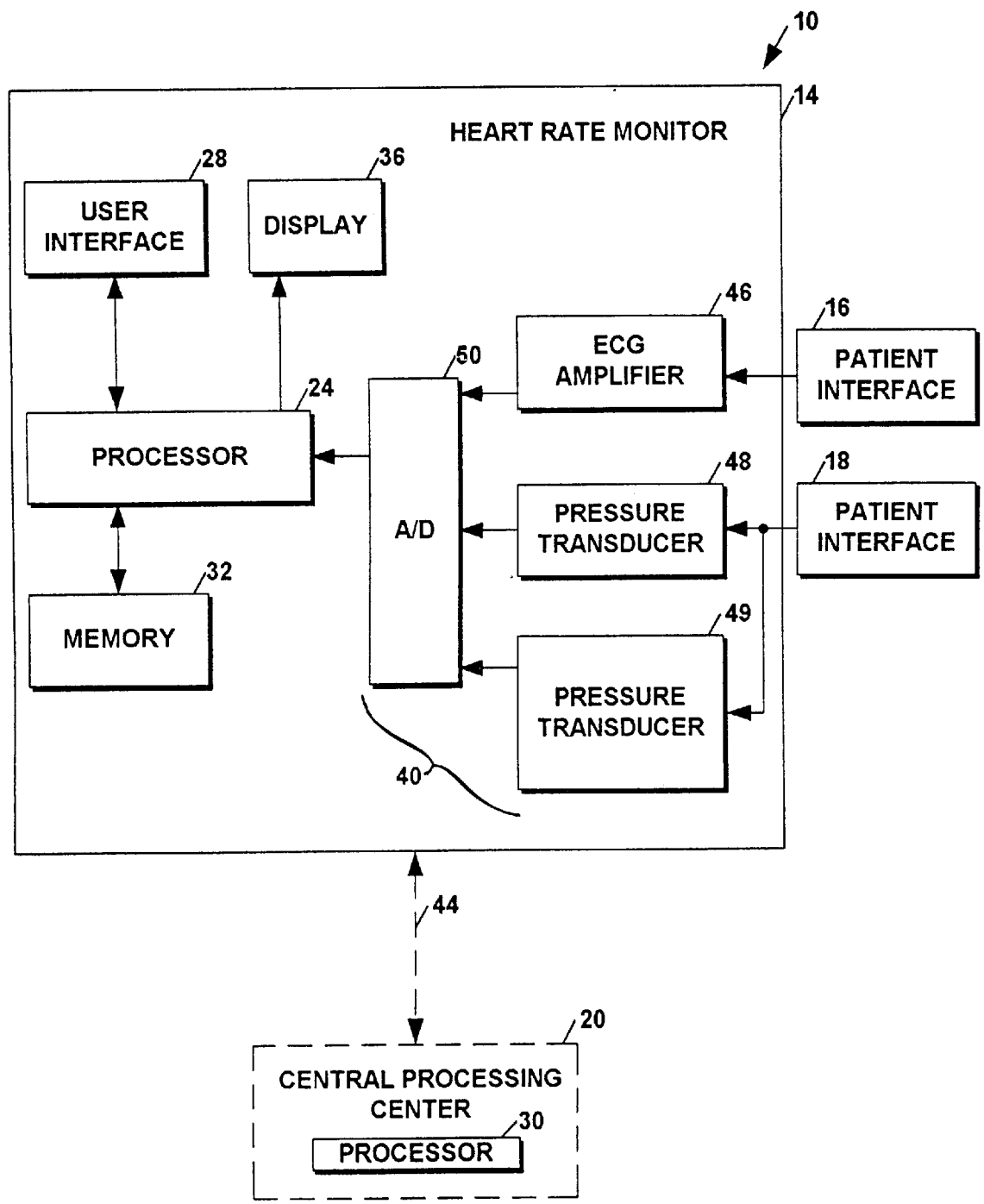
FIG. 1 is a block diagram of a heart rate monitor system providing an indicator of a patient's autonomic nervous system function according to the invention.

Referring to FIG. 1, a heart rate monitor system 10 includes a heart rate monitor 14, patient interfaces 16, 18 and an optional central processing center 20 including a processor 30. The heart rate monitor 14 includes a processor 24, a user interface 28, a memory 32, a display 36 and data acquisition elements 40. The heart rate monitor system 10 is operable to analyze the variability of a patient's heart rate in response to measured physiological data of the patient and to provide an indicator of the patient's autonomic nervous system function, as will be described. The signal processing by which the autonomic function indicator is provided may be performed by the heart rate monitor processor 24, the central processing center processor 30, or by a combination of the two processors.

It is contemplated that the heart rate monitor 14 be located in a physician's office and that the central processing center 20 be located some distance from the physician's office. In one illustrative heart rate monitor system 10, preliminary heart rate variability analysis is performed by the processor 24 at the physician's office and more extensive analysis, including computation of the autonomic function indicator of the invention, is performed remotely, by the processor 30 at the central processing center 20.

The heart rate monitor 14 is coupled to the central processing center 20 by a communication connection 44 which includes the public telephone system and may be implemented with various types of hard-wire or wireless media and may further include one or more public or private networks, such as a local area network (LAN) or a wide area network (WAN) which may be part of the Internet. In one preferred embodiment, the communication connection 44 includes a modem and a radio frequency (RF) connection. The RF connection allows the operator of the monitor 14 to move the monitor without requiring a hard-wire connection to a telephone line.

Processors 24, 30 execute programming instructions by which a patient's heart rate variability is analyzed in response to measured physiological data, such as an ECG signal, and may take various forms, such as conventional microprocessors of a standard personal computer, workstation or other microprocessor-driven device. As one example, the processors 24, 30 are INTEL-compatible microprocessors of IBM-compatible personal computers running the MICROSOFT WINDOWS graphical user interface. In fact, the heart rate monitor 14 and/or the central processing center 20 may be implemented using a standard personal computer chassis with certain components (e.g. ECG monitor 46 and pressure transducers 48, 49) provided in the form of circuit modules adapted for insertion into I/O ports of the computer. A modem at the heart rate monitor 14 permits a dial-up connection to be established with the processing center 20.

The memory 32 includes a Random Access Memory (RAM) for temporary data storage and a device with read/write access for permanent data storage, such as a hard drive. The user interface 28 may be provided by a number of conventional devices, such as a keyboard, touch screen, and/or mouse. In one illustrative embodiment, the user interface 28 includes a touch screen incorporated into the display 36 and the display is a flat panel LCD display. It will be appreciated by those of ordinary skill in the art that the techniques of the present invention may be implemented with various apparatus, both hardware and software.

The data acquisition components 40 of the heart rate monitor 14 include an ECG amplifier 46, a first pressure transducer 48 for measuring the pressure at which the patient breathes for use in connection with the Valsalva test and a second pressure transducer 49 for measuring the patient's inspiration flow for use in connection with the Expiration/

Inspiration (E/I) test. The ECG amplifier 46 operates with a conventional ECG patient interface 16, such as electrode pads adapted for attachment to a patient's chest, and includes signal processing circuitry for conditioning the measured ECG signal for further processing. One suitable commercially available ECG amplifier is of the type sold by Serena Medical Electronics Co., Inc. of San Jose, Calif. under the product name ECG Isolation Amplifier Module Model ECG-170. The output of the ECG amplifier 46 is converted into a digital signal by an analog-to-digital (A/D) converter 50.

The pressure transducer 48 is coupled to a conventional patient interface 18, such as a mouthpiece into which a patient breathes. The pressure transducer 48 measures the pressure differential across a diaphragm within the mouthpiece to provide a pressure transducer output signal indicative of the pressure at which the patient breathes. The pressure transducer output signal is digitized by the A/D converter 50. The pressure stransducer 49 is coupled to a mouthpiece 18 with one end covered. The pressure transducer 49 provides an output signal indicative of the patient's inspiration flow to the A/D converter The digitized ECG, pressure, and inspiration flow signals are coupled to the processor 24 and optionally also to the central processing center 20. The pressure and inspiration flow signals are used to evaluate the accuracy with which the patient performed the particular tests and may also be used to provide feedback to the patient in order to enhance patient compliance with a particular breathing regimen, as is described in U.S. patent application Ser. No. 08/942,710.

Figure 2:
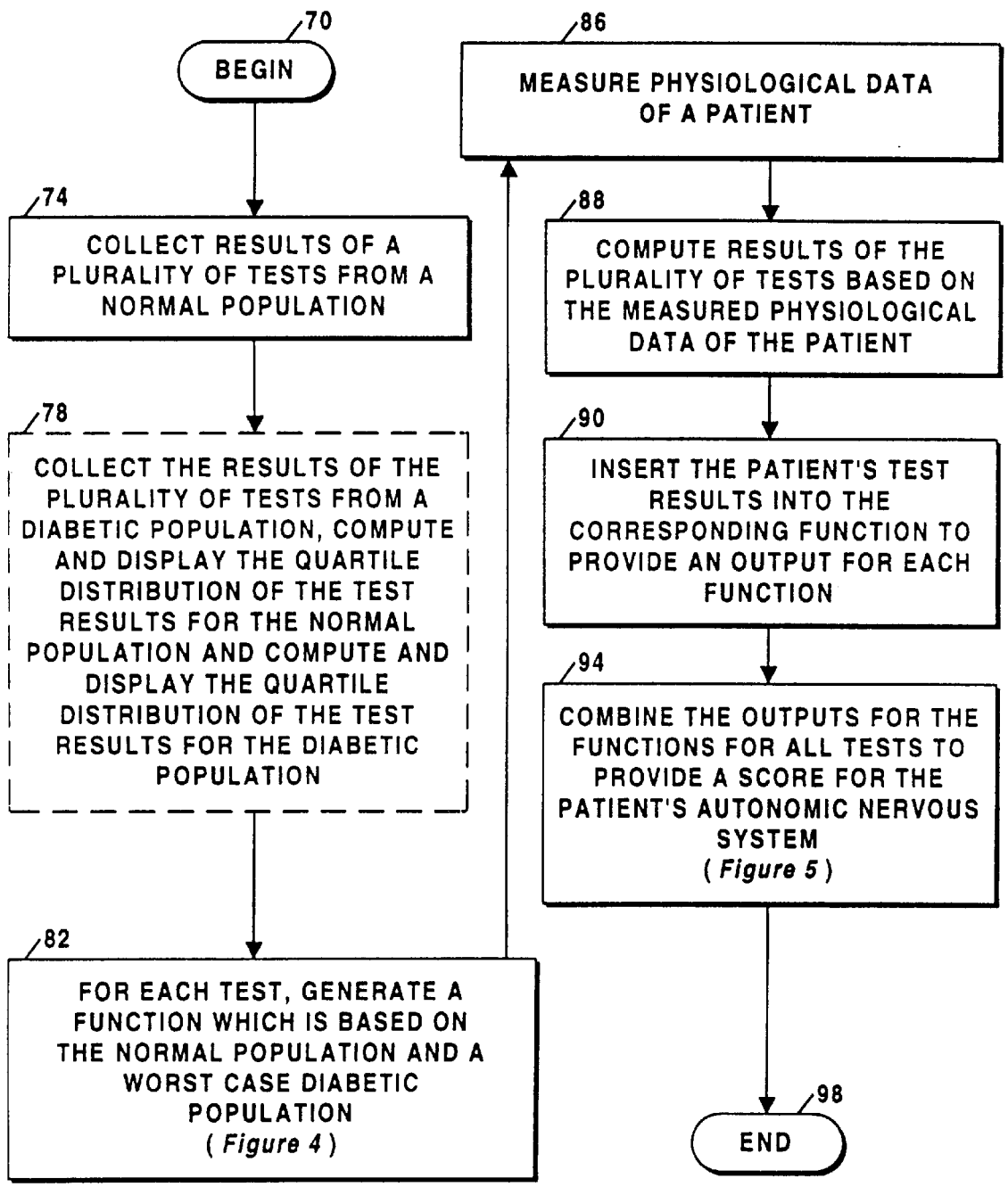
FIG. 2 is a flow diagram illustrating a method of providing the autonomic function indicator of the invention.

Referring also to FIG. 2, a method for providing an indicator of a patient's autonomic nervous system function is illustrated. In general, the method includes preliminary steps 74–82 by which mathematical expressions are generated for a plurality of different autonomic nervous system tests referenced to a cross-sectional population and patient testing steps 86–94 in which physiological data from a particular patient is collected and used to compute the autonomic function indicator of the patient. Since the preliminary process steps 74–82 are not specific to a given patient, these steps may be performed once and the resulting mathematical expressions stored in memory for later use during patient testing.

The method commences at step 70, following which results of a plurality of different conventional autonomic nervous system tests are collected from a normal population (i.e., a population comprising individuals known to be healthy). For purposes of discussion, the invention will be described in connection with the conventional Valsalva and E/I tests. It will be appreciated by those of ordinary skill in the art however, that various other tests or combinations of tests of the autonomic nervous system, such as the Standard Deviation test, the Mean Circular Resultant test, the Coefficient of Variation, the Posture Index, and any other tests, may be performed using the heart rate monitor 14 as shown in FIG. 2 or as modified by the addition of further data acquisition and patient interface components. Further, such other autonomic nervous system tests may be used to provide the indictor of the present invention.

As an optional output of the system 10, the physician or other system operator may be provided with information regarding the results of the conventional tests performed on the normal population and also results of such tests performed on a population known to have autonomic neuropathy (e.g., a diabetic population). It will be appreciated by those of ordinary skill in the art that neuropathy of the autonomic nervous system may stem from complications due to diabetes or various other illnesses. For simplicity of illustration however, a population having autonomic neuropathy will be referred to herein as a diabetic population.

In applications in which it is desired to provide such additional information, in step 78, the results of the autonomic nervous system tests on a diabetic population are collected. In the illustrated embodiment, these test results are processed to determine and display quantile distributions, such as the quartile distributions shown in the box plots of FIG. 3 for the E/I test and in FIG. 3A for the Valsalva test. The median test results are labeled 60*a*, 62*a*, 64*a*, and 66*a*, the maxima are labeled 60*b*, 62*b*, 64*b*, and 66*b*, the minima are labeled 60*c*, 62*c*, 64*c*, and 66*c*, the seventy-fifth percentiles are labeled 60*d*, 62*d*, 64*d*, and 66*d*, and the twenty-fifth percentiles are labeled 60*e*, 62*e*, 64*e*, and 66*e*.

In step 82, for each of the different autonomic nervous system tests, a mathematical expression, or function, is generated which is based on a combination of both the normal and diabetic populations (i.e., a cross-sectional population). The method of generating the mathematical expressions is described below in conjunction with FIG. 4. The result of step 82 is a mathematical expression for the particular test referenced to the cross-sectional population. The mathematical expressions generated in step 82 may be referenced to a portion of the cross-sectional population representing a particular age group, as will be described.

In step 86, physiological data of the patient to be tested is measured. In the illustrative embodiment in which the autonomic nervous system tests are the Valsalva test and the E/I test, the physiological data is the ECG signal provided by the ECG amplifier 46 (FIG. 1) and measured while the patient performs the Valsalva and E/I breathing regimens.

In step 88, the measured data is used to compute the result of each of the plurality of different autonomic nervous system tests. For example, in the illustrative embodiment, the Valsalva ratio is provided by the ratio of the shortest measured R-R interval during the Valsalva breathing maneuver to the longest measured R-R interval at rest and the E/I ratio is provided by a ratio of the average of the heart rate peaks to the average of the heart rate troughs. Thus, step 88 includes detection of R-R intervals from the ECG signal and computation of the respective ratios. Detection of R-R intervals may be achieved by various techniques, such as a simple threshold technique or the more rigorous techniques described in the above-mentioned U.S. Pat. No. 5,984,954.

In step 90, the patient's test results from step 88 for each of the performed autonomic nervous system tests are inserted into the respective mathematical expression in order to yield an output value for each such expression. For example, the patient's Valsalva ratio from step 88 is inserted into the mathematical expression generated in step 82 for the Valsalva test and the patient's E/I ratio from step 88 is inserted into the mathematical expression generated in step 82 for the E/I test. The resulting output value of each mathematical expression provides the test result referenced against the cross-sectional population. In applications in which the cross-sectional population is age limited, the resulting output value of the mathematical expression should be constant with age unless the patient's autonomic nervous system function is degrading as a result of factors other than age. This is because the patient's test results, which will naturally show a degradation in the autonomic nervous system function with age, are referenced against the results of the tests performed on the age-limited cross-sectional population, which test results will also show a corresponding degradation in the autonomic nervous system function with age.

In step 94, the output values of the mathematical expressions for each of the different autonomic nervous system tests are combined in order to provide a composite indictor of the patient's autonomic function, following which the process terminates in step 98. The manner in which the function output values are combined is described in conjunction with FIG. 5.

The resulting indicator provides a highly accurate measure of the autonomic function with a reproducibility on the order of 5%. Since the autonomic nervous system function indicator is a composite measure of autonomic function, errors associated with the performance and evaluation of the individual test results are minimized. Stated differently, the sensitivity of the autonomic nervous system indicator to factors such as test performance variations is minimized as compared to individual test results. Also, the autonomic nervous system function indicator of the present invention provides greater contrast between results of healthy individuals and those with neuropathy, thereby facilitating accurate assessment of test results. Further, the autonomic nervous system indicator is provided in a standard form for standard interpretation regardless of the number of tests performed and provides a convenient tool for long-term tracking of patient's autonomic nervous system function.

Figure 4:
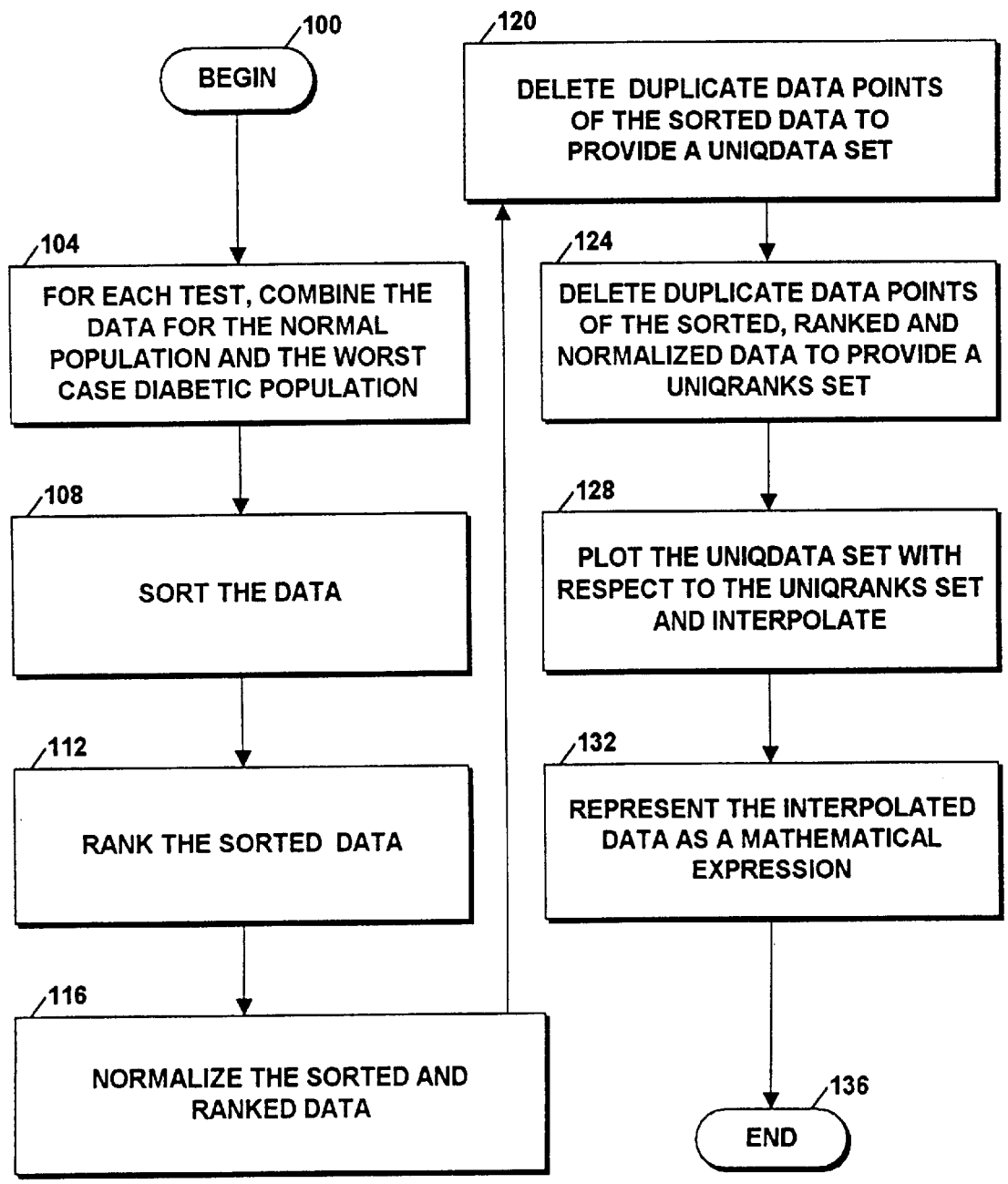
FIG. 4 is a flow diagram illustrating a method of generating a mathematical expression for use in the method of FIG. 2.

Referring to FIG. 4, a method for generating a mathematical expression for each of a plurality of different autonomic nervous system tests is illustrated. Process steps 104–132 are repeated for each autonomic nervous system test used to compute the autonomic function indicator. The method of FIG. 4 will be described in connection with an example based on the E/I test.

The process begins at step 100, following which data for a normal population and a diabetic population are combined. The data is comprised of results of the plurality of different autonomic nervous system tests performed on the respective population. The result of the combination step 104 is a database containing test results of members of a cross-sectional population in a format which can be read and manipulated in subsequent steps.

In the illustrative embodiment in which the autonomic function indicator is a function of the Valsalva and E/I tests, the format of the data provided in step 104 is a 2×n matrix. Each of the two columns corresponds to one of the tests and the value n is indicative of the number of individuals comprising the cross-sectional population (i.e., the number of data points in the data set). In one illustrative embodiment, the database is a 2×480 matrix comprising data for 240 healthy individuals and 240 diabetic individuals.

The diabetic data contained in the database provided in step 104 may be the results of the autonomic nervous system tests performed on diabetic individuals or, alternatively, may be provided in the form of worst case data for this population, as is preferred. More particularly, the worst cases of diabetic neuropathy result in little or no heart rate variability in response to the autonomic nervous system tests, such as the Valsalva test and the E/I test. Thus, the worst case result of these tests is the value 1, since the measured R-R intervals would be unchanged. Use of this "worst case" diabetic data minimizes certain errors due to the test results of some neuropathy patients who respond like a healthy individual to one autonomic nervous system test, but respond like a diabetic individual to another.

Figure 4A:
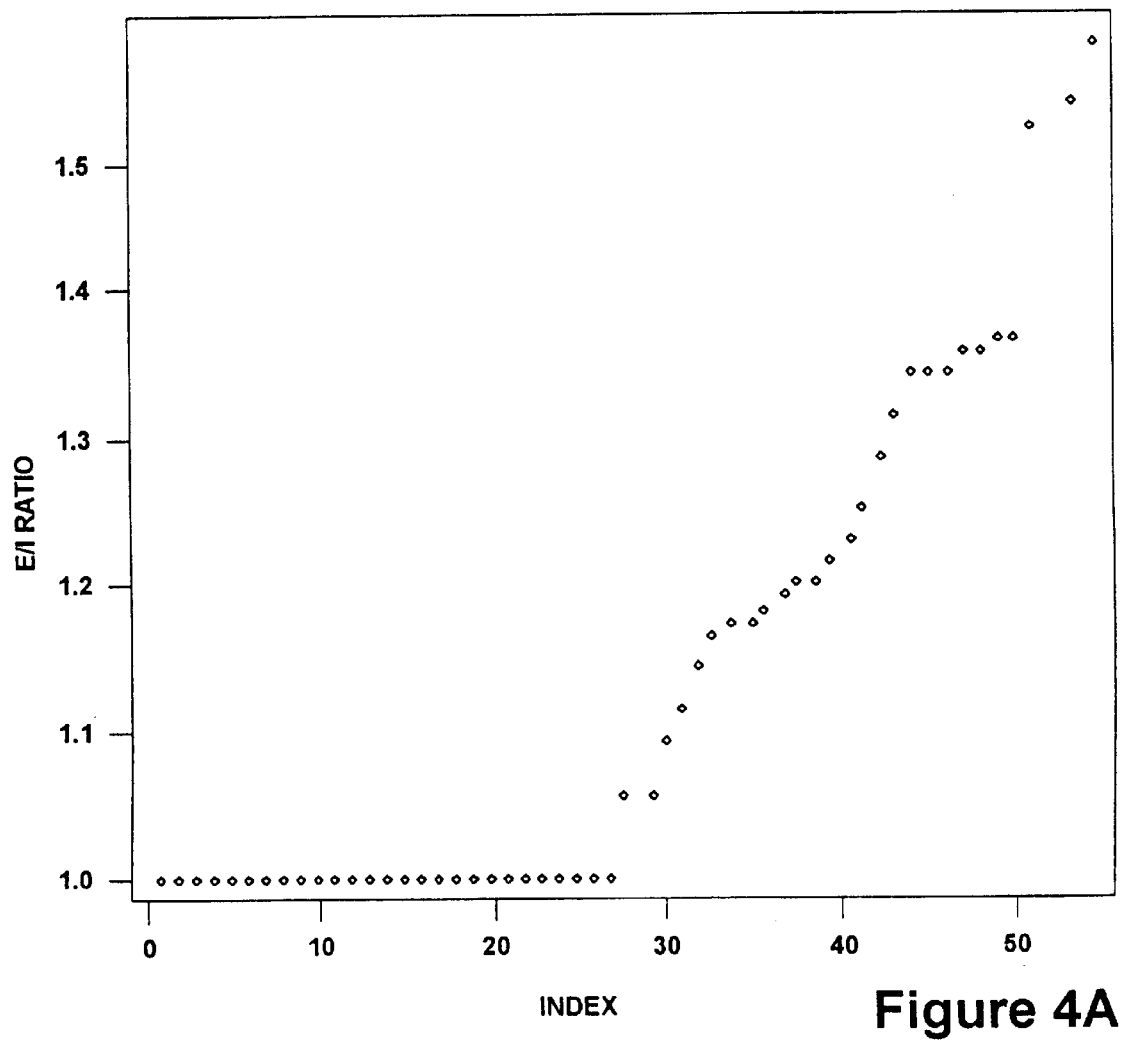
FIG. 4A is a plot showing an example of sorted E/I test data.

In step 108, for each test, the data is sorted, in the illustrative embodiment, from least to greatest value. In the illustrative E/I test example, the sorted data is shown in FIG. 4A and consists of the following E/I test results: 1.00, 1.00, 1.00, 1.00, 1.00, 1.00, 1.00, 1.00, 1.00, 1.00, 1.00, 1.00, 1.00, 1.00, 1.00, 1.00, 1.00, 1.00, 1.00, 1.00, 1.00, 1.00, 1.00, 1.00, 1.00, 1.00, 1.00, 1.05, 1.05, 1.09, 1.11, 1.14, 1.16, 1.17, 1.17, 1.18, 1.19, 1.20, 1.20, 1.21, 1.23, 1.25, 1.29, 1.32, 1.35, 1.35, 1.35, 1.36, 1.36, 1.37, 1.37, 1.52, 1.53, 1.55.

In step 112, the data for each test is ranked. Ranking assigns a value to each data point according to its value relative to the lowest and highest values of the data set. More particularly, the lowest data point in the set is assigned a value of 1 and the highest data point in the set is assigned a value equal to the number of entries in the data set. If two or more entries in the data set have the same value, then each is assigned a rank equal to the average of the ranks that the entries would have been assigned had they not been equal. As a simple example of the ranking process, if the data set contains the data points 1, 1, 2, and 5, then the resulting ranks are 1.5, 1.5, 3, and 4, respectively. This is because, had there not been two equal values, the resulting ranks would have been 1, 2, 3, and 4, respectively. The two occurrences of value 1 are then assigned a value equal to the average of the ranks that these entries would have been assigned had they not been equal, or the average of 1+2=1.5.

Figure 4B:
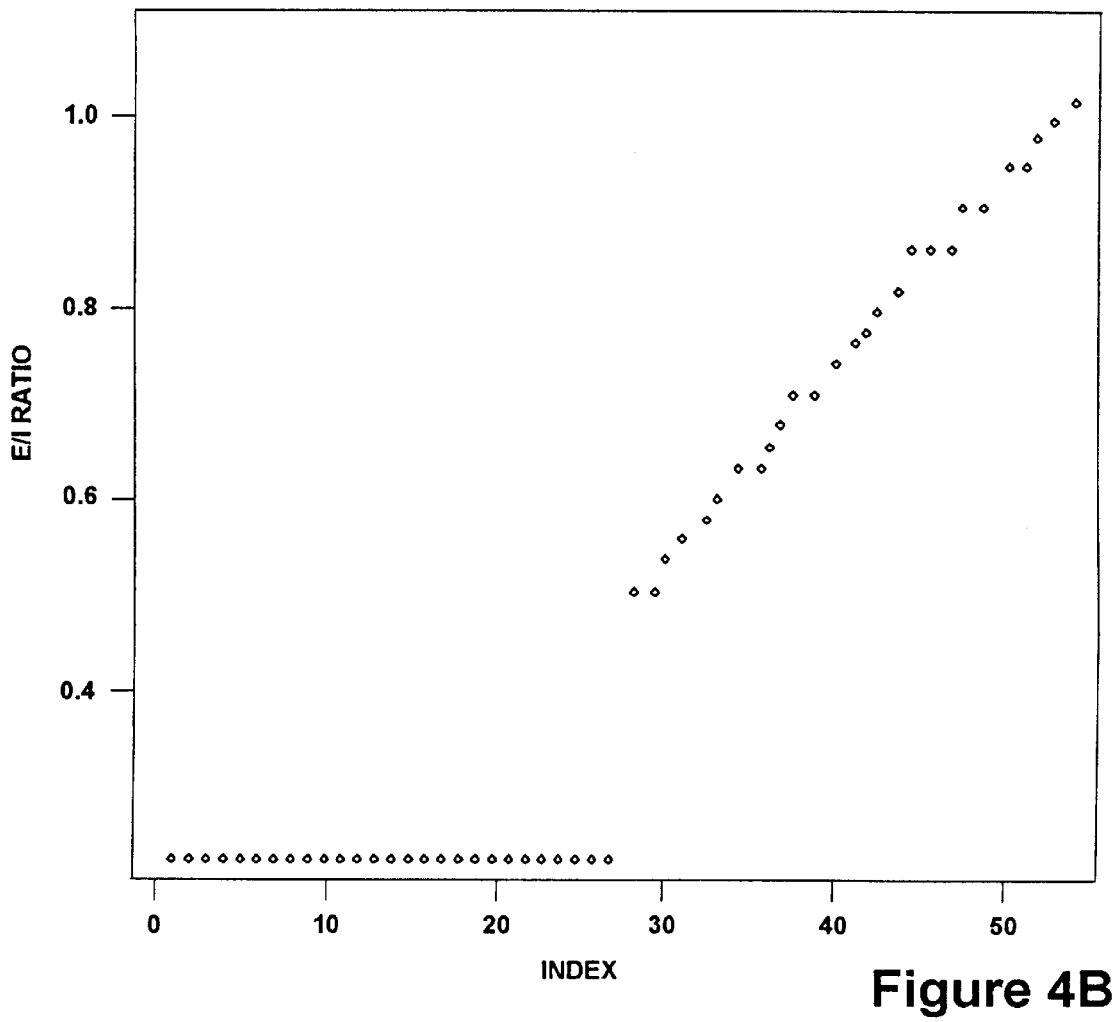
FIG. 4B is a plot showing the data of FIG. 4A after the data has been ranked.

In step 116, the ranked data for each test is normalized to a value of one by dividing each data point by the total number of data points in the set. It will be appreciated by those of ordinary skill in the art that certain process steps may be combined. As one example, the ranking of step 112 may be combined with the normalizing of step 116 into a single process step. In the illustrative example, the ranked and normalized data is shown in FIG. 4B and includes the following data points: 0.2592593, 0.2592593, 0.2592593, 0.2592593, 0.2592593, 0.2592593, 0.2592593, 0.2592593, 0.2592593, 0.2592593, 0.2592593, 0.2592593, 0.2592593, 0.2592593, 0.2592593, 0.2592593, 0.2592593, 0.2592593, 0.2592593, 0.2592593, 0.2592593, 0.2592593, 0.2592593, 0.2592593, 0.2592593, 0.2592593, 0.2592593, 0.5277778, 0.5277778, 0.5555556, 0.5740741, 0.5925926, 0.6111111, 0.6388889, 0.6388889, 0.6666667, 0.6851852, 0.7129630, 0.7129630, 0.7407407, 0.7592593, 0.7777778, 0.7962963, 0.8148148, 0.8518519, 0.8518519, 0.8518519, 0.8981481, 0.8981481, 0.9351852, 0.9351852, 0.9629630, 0.9814815, 1.0000000.

Figure 4C:
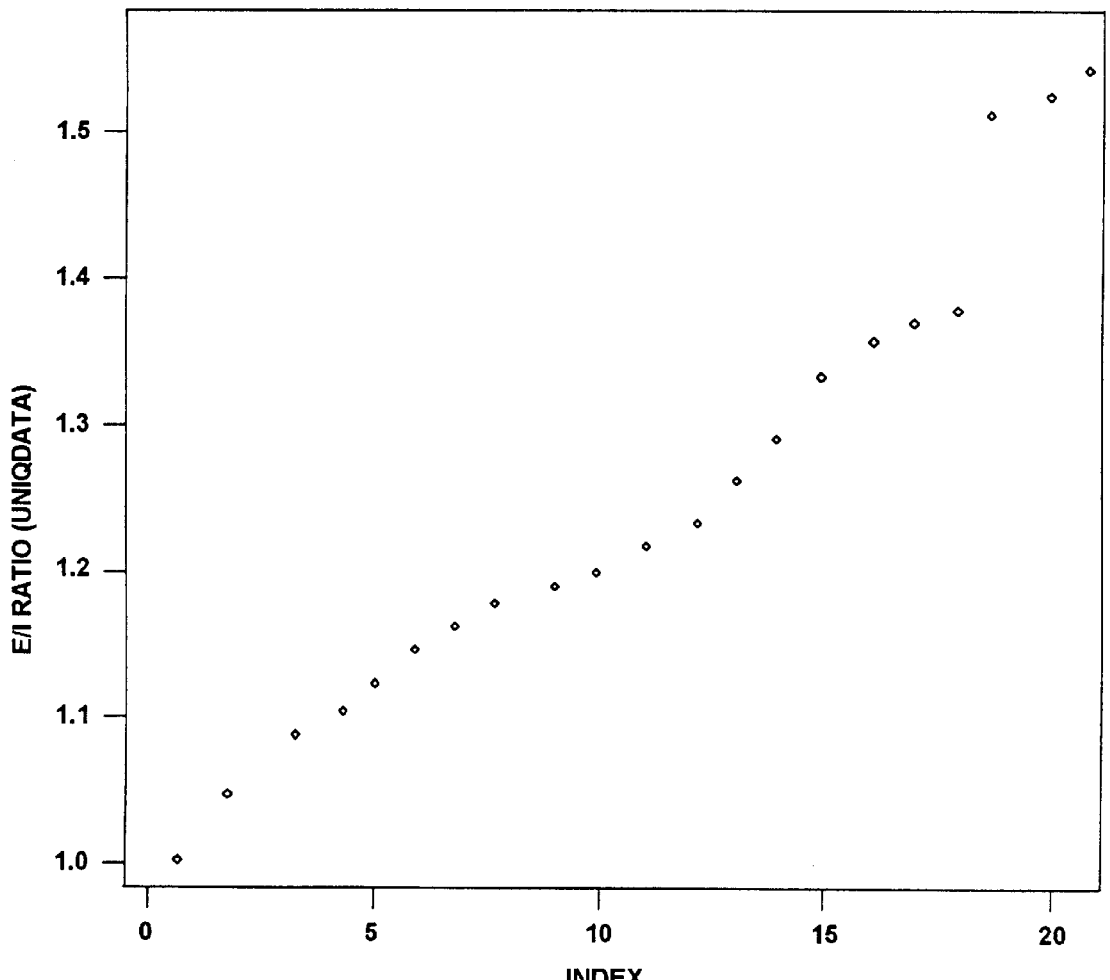
FIG. 4C is a plot showing the data of FIG. 4A with duplicate data points removed.

In step 120, duplicate data points of the sorted data for each test are identified and removed to provide a UNIQ-DATA set. In the illustrative example, the UNIQDATA set is shown in FIG. 4C and the data points are as follows: 1.00, 1.05, 1.09, 1.11, 1.14, 1.16, 1.17, 1.18, 1.19, 1.20, 1.21, 1.23, 1.25, 1.29, 1.32, 1.35, 1.36, 1.37, 1.52, 1.53, 1.55.

Figure 4D:
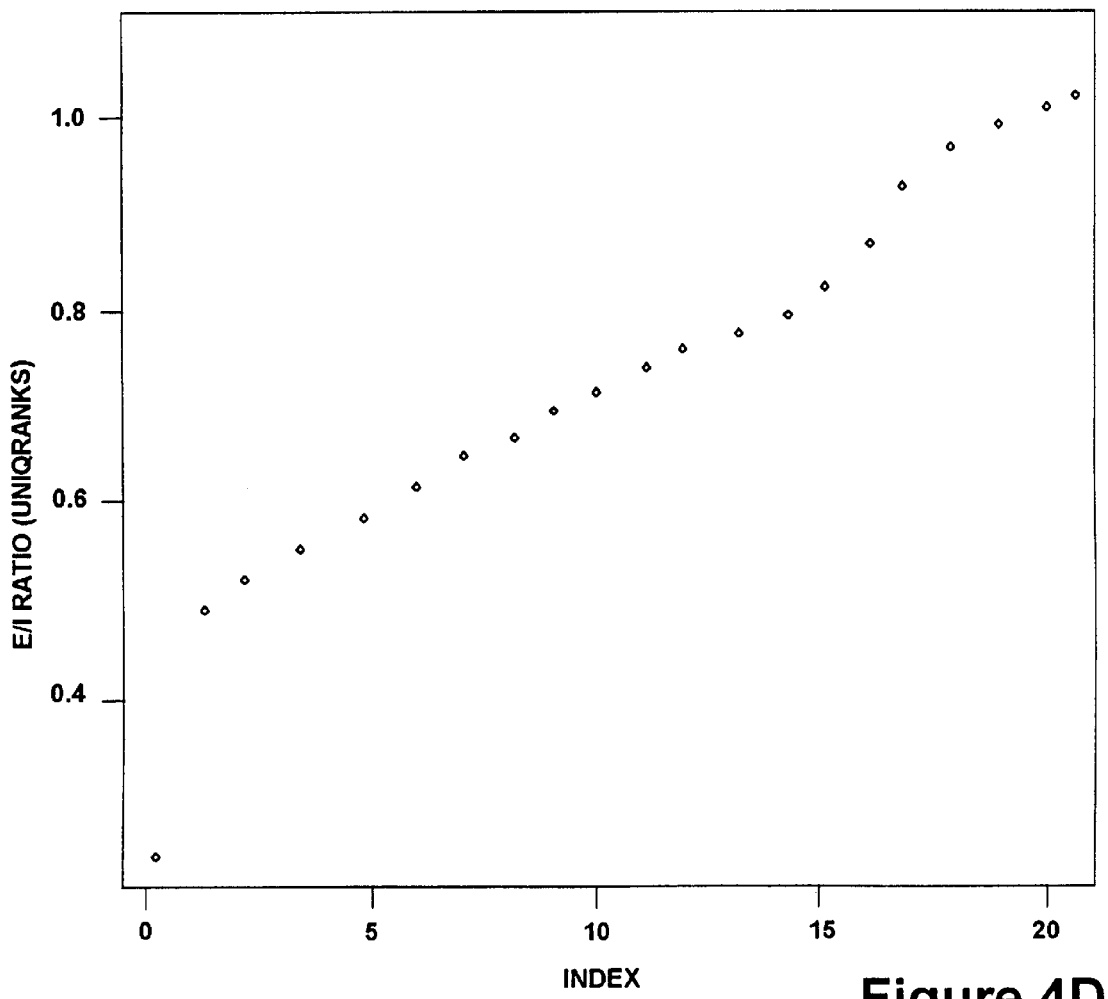
FIG. 4D is a plot showing the data of FIG. 4B with duplicate data points removed.

In step 124, duplicate data points of the normalized data for each test are identified and removed to provide a UNIQRANKS set. In the illustrative example, the UNIQRANKS set is shown in FIG. 4D and the data points are as follows: 0.2592593, 0.5277778, 0.5555556, 0.5740741, 0.5925926, 0.6111111, 0.6388889, 0.6666667, 0.6851852, 0.7129630, 0.7407407, 0.7592593, 0.7777778, 0.7962963, 0.8148148, 0.8518519, 0.8981481, 0.9351852, 0.9629630, 0.9814815, 1.0000000.

Figure 4E:
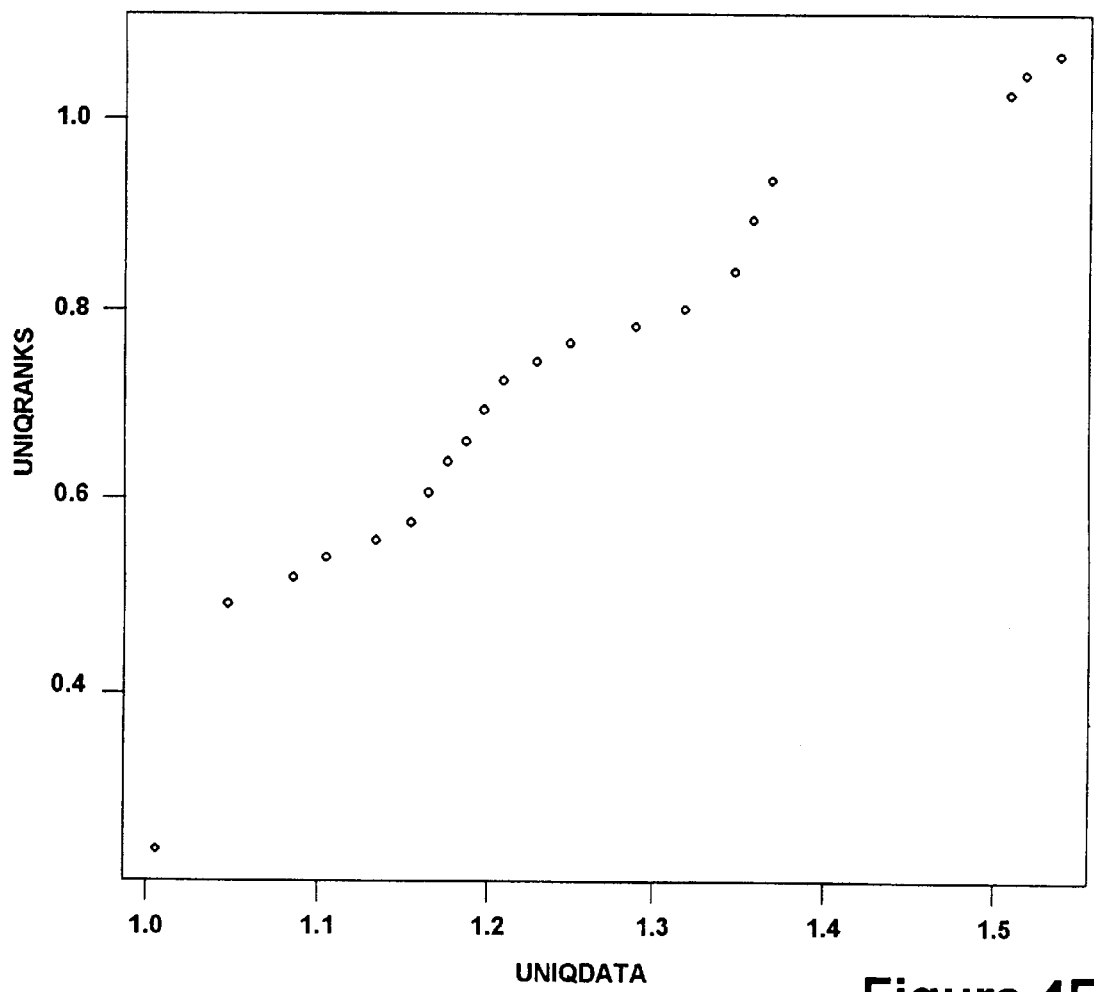
FIG. 4E is a plot of the data of FIG. 4C versus the data of FIG. 4D.

In step 128, the resulting data sets are plotted with respect to each other and the data is interpolated. In the illustrative embodiment, the y axis represents the UNIQRANKS set and the x axis represents the UNIQDATA set. In the illustrative example, the resulting plot is shown in FIG. 4E.

Figure 4F:
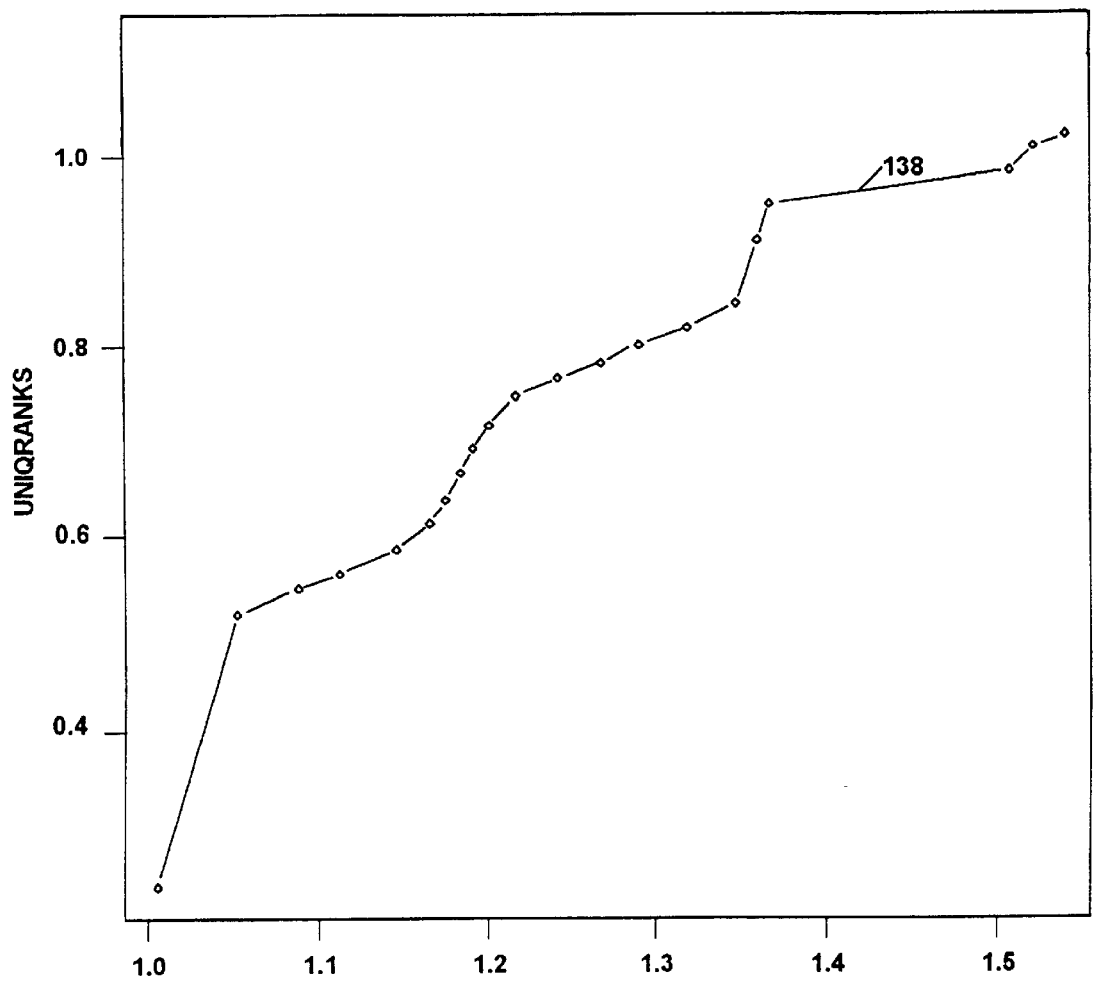
FIG. 4F illustrates a linear interpolation of the data of FIG. 4E.

Various interpolation schemes are possible, such as linear interpolation and polynomial interpolation. Preferably, the selected interpolation scheme produces a non-decreasing function consistent with the non-decreasing relationship between the test results and rank. In the illustrative embodiment, the data points are fitted to a straight line function (i.e., linear interpolation). In the illustrative example, the plot resulting from linear interpolation is shown in FIG. 4F.

The resulting straight line provided by the interpolation of step 128 is represented in the form of a mathematical expression in step 132, following which the process ends in step 136. Thus, in the illustrative embodiment, in which the data is linearly interpolated in step 128, the resulting mathematical expression is of the form: y=mx+b, where x and y are variables and m and b are constants which are a function of the cross-sectional population. It will be appreciated by those of ordinary skill in the art that the populations on which the mathematical expressions are based can be readily varied, as may be desirable to account for variations in test results of the normal population over time and over geographical regions.

Output values for the mathematical expressions generated by the process of FIG. 4 are provided for a particular patient in step 90 of FIG. 2 by inserting the autonomic nervous system test results of the patient (from step 88 in FIG. 2) into the corresponding mathematical expressions (generated in step 82 in FIG. 2). For example, in the illustrative embodiment, the patient's Valsalva ratio computed in step 88 provides the variable x for use in the y=mx+b expression derived for the Valsalva test in step 82 in order to provide the output value y for the function. Since the linear interpolation results in a series of interconnected line segments, a plurality of mathematical expressions are provided, each having a different slope and y-intercept. The particular mathematical expression (i.e., the values of slope, m and y-intercept, b) are a function of the particular line segment corresponding to the patient's Valsalva ratio. For example, in the case where the patient's Valsalva ratio is 1.45, the mathematical expression is provided by the line segment labeled 138 in FIG. 4F and given by y=(0.2)(x−1.36)+0.87. Inserting the patient's Valsalva ratio as the x variable, provides the output value of y=(0.2)(1.45−1.36)+0.87, or 0.888. Similarly, the patient's E/I ratio is inserted into the y=mx+b expression derived for the E/I test in order to arrive at the y output value for that function.

In a preferred embodiment, the cross-sectional data collected and combined in process step 104 is age-limited and the process of FIG. 4 is repeated for each of several age groups in order to generate a plurality of mathematical expressions for each of the plurality of different autonomic nervous system tests, with each expression corresponding to a different age group. When a patient is tested, the mathematical functions corresponding to the patient's age are used to generate the autonomic function indicator. In this way, the natural degradation of the autonomic nervous system which occurs with age does not affect the indicator.

Figure 5:
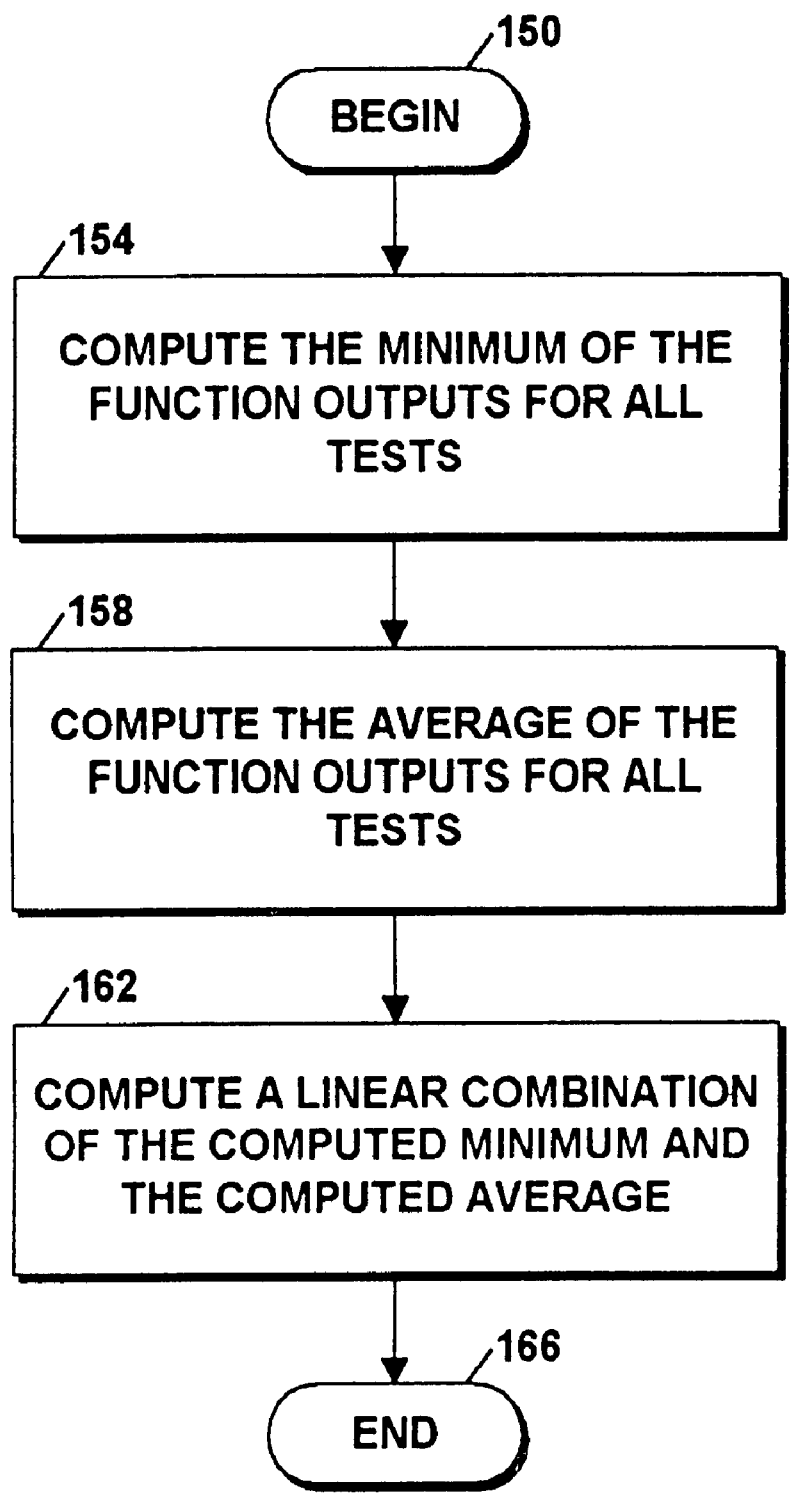
FIG. 5 is a flow diagram illustrating a method of combining the output values of a plurality of mathematical expressions for use in the method of FIG. 2.

Referring also to FIG. 5, a method of combining the output values for each function provided in step 90 of FIG. 2 is illustrated. The process begins in step 150, following which the output values of the mathematical expressions for the plurality of different autonomic nervous system tests are analyzed to determine the minimum value. Use of the minimum value in the process of FIG. 5 presumes that all of the autonomic nervous system tests used to provide the indicator are such that a low test score is indicative of neuropathy. In applications in which one or more autonomic nervous system tests used to provide the indicator are such that a high test score is indicative of neuropathy, such test results are processed prior to generation of the corresponding mathematical expression in order to provide a result in which the neuropathetic results are lower than normal results. As one example, consider the case where the result of an autonomic nervous system test of a healthy individual is given by the value 40 and that of a diabetic individual is given by the value 80. In this case, the scale of these test results can be inverted by multiplying the test result by −1 and adding the value 120 to the product. The test result for the healthy individual then becomes (−1)(40)+120=80 and that of the diabetic individual becomes (−1)(80)+120=40.

In step 158, the same output values of the mathematical expressions for the plurality of different autonomic nervous system tests are analyzed to compute the average value In step 162, the minimum determined in step 154 and the average determined in step 158 are linearly combined to provide the autonomic function indicator according to the invention, following which the process ends in step 166. More particularly, each of the average and minimum values are multiplied by a predetermined coefficient having a value between 0 and 1 before being combined as follows: (coefficient)(minimum)+(1−coefficient)(average)=indicator. In one illustrative embodiment, the predetermined coefficient is given by 0.5. However, it will be appreciated by those of ordinary skill in the art that the coefficient may be varied in order to vary the significance (i.e., weighting) of the minimum and average values in the resulting indicator. For example, if all tests comprising the autonomic function indicator are found to be equally accurate representations of neuropathy, then it may be desirable to emphasize the average in the resulting indicator; whereas, if one test is found to represent neuropathy better than others, it may be desirable to emphasize the minimum in the resulting indicator since averaging would dilute the effects of neuropathy.

Thus, the autonomic function indicator is a single value measure of the patient's autonomic nervous system function which is based on two or more different measures of the autonomic nervous system referenced to the cross-sectional population. In the illustrative embodiment, the autonomic indicator is has a value between zero and one, with lower values being more indicative of neuropathy than higher values.

It will be appreciated by those of ordinary skill in the art that, if one of the autonomic nervous system tests is determined to be a more valuable autonomic function indicator than other tests making up the indicator, the individual test results may be appropriately weighted in order to emphasize the relative importance of the tests.

Figure 6:
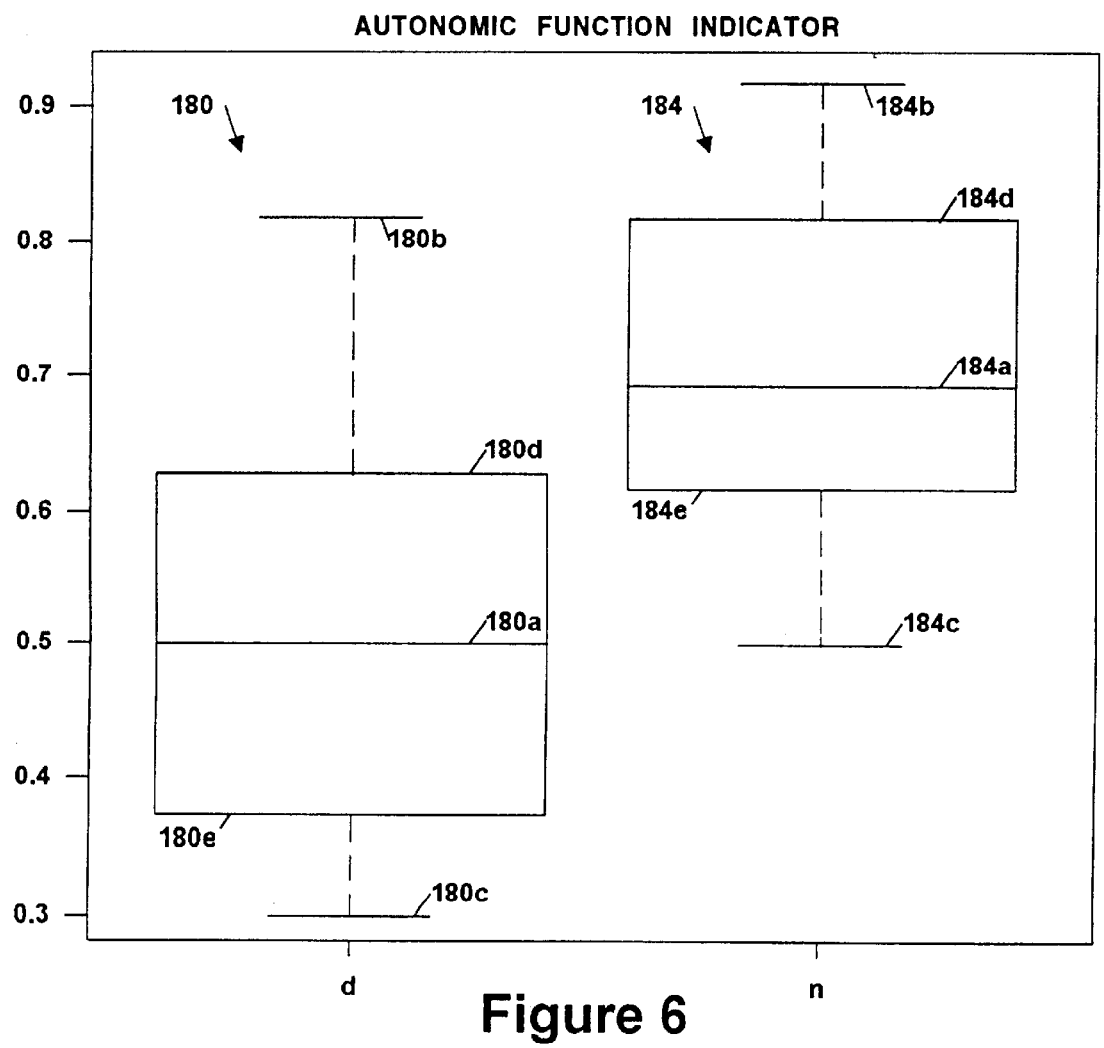
FIG. 6 contains box plots illustrating the autonomic function indicator of the invention for both normal and diabetic populations.

Referring to FIG. 6, box plots 180, 184 showing the autonomic indictor for both normal and diabetic populations, respectively, are shown. The median autonomic indicators are labeled 180a, 184a, the maxima are labeled 180b, 184b, the minima are labeled 180c, 184c, the seventy-fifth percentiles are labeled 180d, 184d, and the twenty-fifth percentiles are labeled 180e, 184e.

Figure 3:
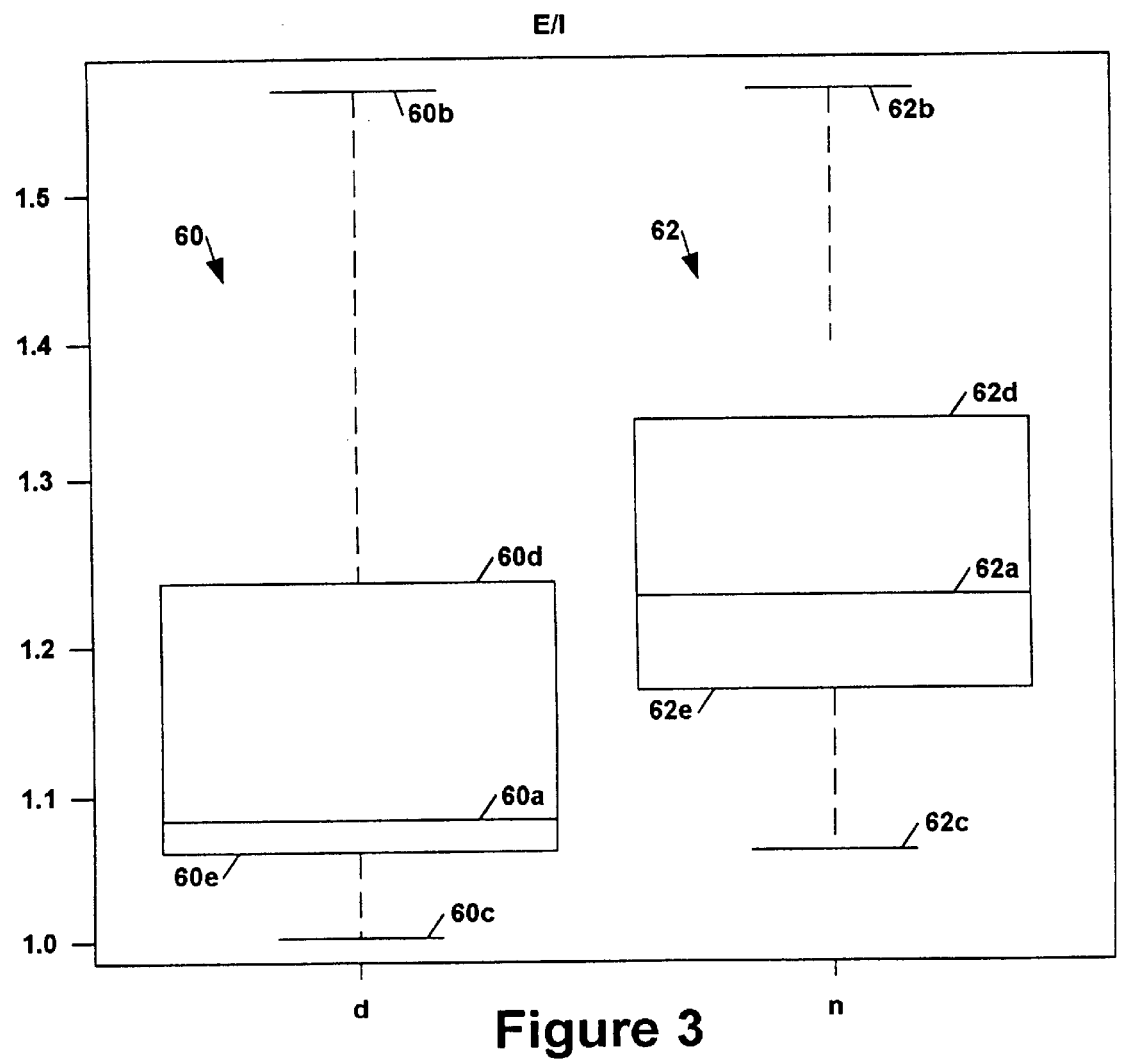
FIG. 3 contains box plots illustrating E/I ratios of normal and diabetic populations.
Figure 3A:
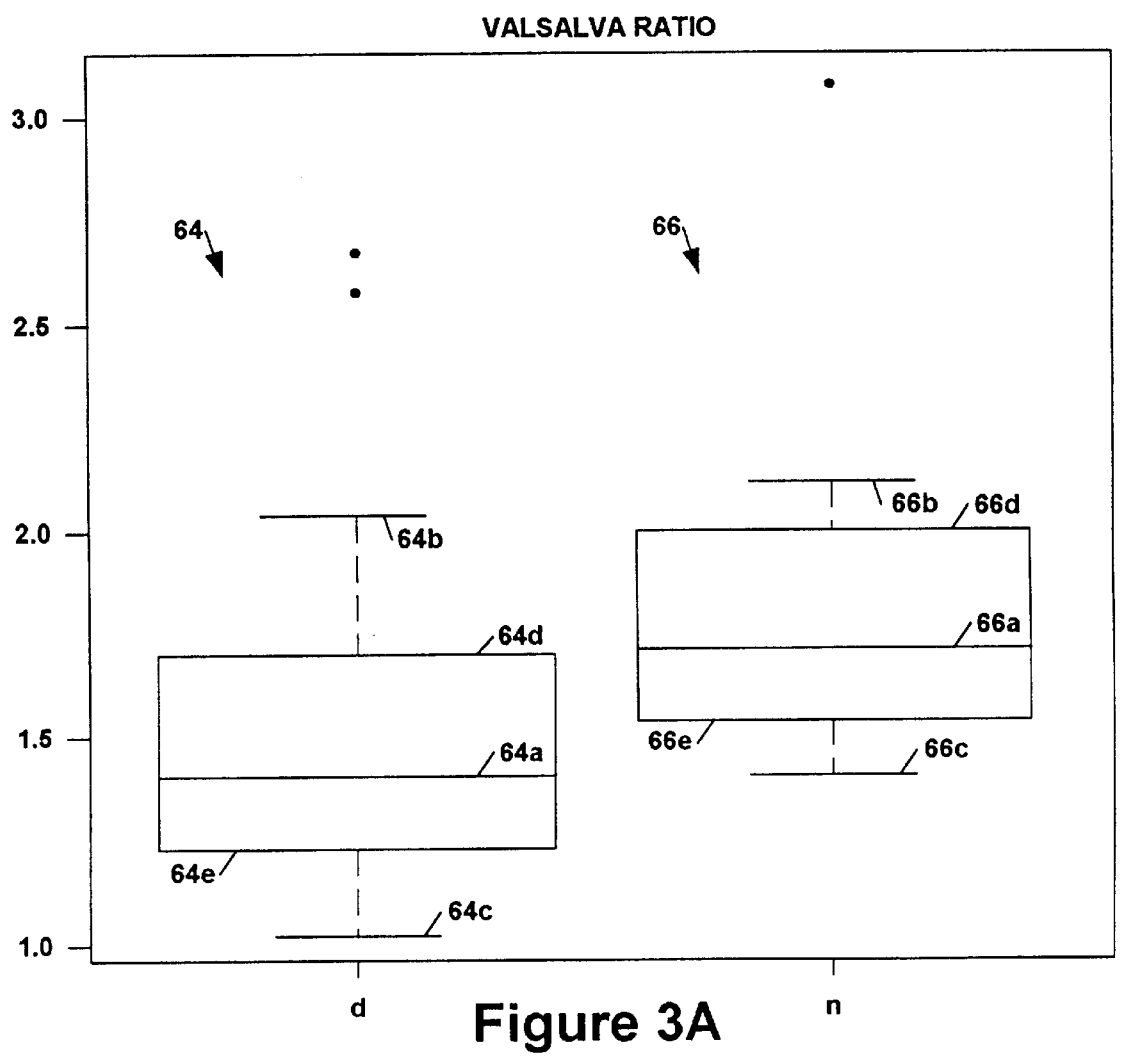
FIG. 3A contains box plots illustrating Valsalva ratios of normal and diabetic populations.

Consideration of the autonomic indictor plots of FIG. 6 with respect to the Valsalva ratio plots of FIG. 3 and the E/I ratio plots of FIG. 3A reveals that the autonomic indicator provides greater contrast between healthy and diabetic individuals, thereby facilitating interpretation of the autonomic indicator. Thus, it is generally easier to characterize a patient as having autonomic neuropathy based on the autonomic function indicator of the invention, since there is relatively little overlap in the autonomic indicators for the two populations.

Having described the preferred embodiments of the invention, it will now become apparent to one of ordinary skill in the art that other embodiments incorporating their concepts may be used.

It is felt therefore that these embodiments should not be limited to disclosed embodiments but rather should be limited only by the spirit and scope of the appended claims. All publications and references cited herein are expressly incorporated herein by reference in their entirety.

What is claimed is:

1. A method of indicating the autonomic nervous system function of a patient, comprising the steps of:

measuring physiological data of the patient;

determining an output value for each of a plurality of different tests of the autonomic nervous system in response to said measured physiological data of the patient and physiological data of a population; and combining the output values for each of said plurality of tests to provide an indicator of the patient's autonomic nervous system function.

2. The method of claim 1 wherein said plurality of different tests of the autonomic nervous system comprise the Valsalva test and the E/I test.

3. The method of claim 1 wherein said output value combining step comprises the steps of:

determining a minimum of the output values for each of the plurality of tests;

determining an average of the output values for each of the plurality of tests; and computing a weighted average of said minimum and said average.

4. The method of claim 1 wherein said population comprises healthy individuals and diabetic individuals.

5. The system of claim 1 wherein said indicator of the patient's autonomic nervous system function is a numerical value.

6. A method of indicating the autonomic nervous system function of a patient, comprising the steps of:

measuring physiological data of the patient;

determining an output value for each of a plurality of different tests of the autonomic nervous system in response to said measured physiological data of the patient and physiological data of a population, wherein said output value determining step comprises the steps of:

generating a mathematical expression for each of the plurality of tests of the autonomic nervous system as a function of said physiological data of said population; and inserting said measured physiological data of the patient into said mathematical expression for each of the plurality of tests to provide said output value for each of said plurality of tests; and combining the output values for each of said plurality of tests to provide an indicator of the patient's autonomic nervous system function.

7. The method of claim 6 wherein said mathematical expression generating step comprises generating a plurality of mathematical expressions for each of said plurality of tests of said autonomic nervous system, with each one of said plurality of mathematical expressions corresponding to a different age group.

8. The method of claim 6 wherein said mathematical expression generating step comprises, for each mathematical expression, the steps of:

sorting the physiological data from said population to provide sorted data;

ranking the sorted data to provide ranked data;

normalizing the ranked data to provide normalized data;

plotting the sorted data with respect to said normalized data;

interpolating the plotted data; and representing the interpolated data as the mathematical expression.

9. The method of claim 8 wherein said interpolating step comprises the step of linearly interpolating the plotted data and said representing step comprises the step of representing the interpolated data as a line function.

10. A method of assessing the function of a patient's autonomic nervous system, comprising the steps of:

generating a plurality of mathematical expressions, each one associated with a different test of the autonomic nervous system and based on physiological data of a population;

measuring physiological data of the patient;

inserting the measured physiological data into each of the plurality of mathematical expressions to provide an output value for each of the plurality of mathematical expressions; and combining the output values for each of the plurality of mathematical expressions to provide an indicator of the patient's autonomic nervous system function.

11. The method of claim 10 wherein said plurality of tests of the autonomic nervous system comprise the Valsalva test and the E/I test.

12. The method of claim 10 wherein, for each different test of said autonomic nervous system, a plurality of mathematical expressions are generated, with each one corresponding to a different age group.

13. The method of claim 10 the step of generating a plurality of mathematical expressions comprises, for each mathematical expression, the steps of:

sorting the physiological from said population to provide sorted data;

ranking the sorted data to provide ranked data;

normalizing the ranked data to provide normalized data;

plotting the sorted data with respect to the normalized data;

interpolating the plotted data; and representing the interpolated data as the mathematical expression.

14. The method of claim 13 wherein said interpolating step comprises the step of linearly interpolating the plotted data and said representing step comprises the step of representing the interpolated data as a line function.

15. The method of claim 10 wherein said population comprises healthy individuals and diabetic individuals.

16. The method of claim 10 wherein said step of combining the output values for each of the plurality of mathematical expressions comprises the steps of:

determining a minimum of the output values for each of the plurality of mathematical expressions, determining an average of the output values for each of the plurality of mathematical expressions; and computing a weighted average of said minimum and said average to provide said indicator of the patient's autonomic nervous system function.

17. A system for providing an indicator a patient's autonomic nervous system function comprising:

a patient interface for measuring physiological data of the patient;

a database containing physiological data of a population; and a processor operative to compute a result for each of a plurality of different autonomic nervous system tests in response to said physiological data of the patient and said physiological data of the population and to combine said results for each of said plurality of autonomic nervous system tests to provide said indicator of the patient's autonomic nervous system function.

18. The system of claim 17 wherein said indicator of the patient's autonomic nervous system function is a numerical value.

19. The system of claim 17 wherein said processor is operative to generate a mathematical expression for each of said plurality of tests as a function of said physiological data of said population and to insert said measured physiological data of the patient into said mathematical expression for each of said plurality of tests to compute said result for each of said plurality of tests.

20. The system of claim 17 wherein said database contains physiological data of said population grouped by age and said processor is operative to compute a result for each of said plurality of different autonomic nervous system tests in response to physiological data of the patient and a portion of said physiological data of said population corresponding to the age of the patient.

21. The system of claim 17 wherein said patient interface comprises an ECG monitor and a circuit for measuring R-R intervals of the patient.

22. The system of claim 17 wherein said database contains physiological data of a population comprising healthy individuals and diabetic individuals.

23. The system of claim 17 further comprising a display for displaying a distribution of said indicator computed for members of said population.

* * * * *

UNITED STATES PATENT AND TRADEMARK OFFICE
CERTIFICATE OF CORRECTION

PATENT NO. : 6,416,473 B1
DATED : July 9, 2002
INVENTOR(S) : Risk et al.

It is certified that error appears in the above-identified patent and that said Letters Patent is hereby corrected as shown below:

Column 5,
Line 59, reads "indictor" and should read -- indicator --.

Column 6,
Line 38, reads "to and the E/I" and should read -- and the E/I --.

Column 7,
Line 3, reads "indictor" and should read -- indicator --.

Column 10,
Line 38, reads "is has a" and should read with -- has a --.
Lines 48 and 54, reads "indictor" and should read -- indicator --.

Column 12,
Line 32, reads "claim 10 the step" and should read -- claim 10 wherein the step --.
Line 35, reads "physiological from" and should read -- physiological data from --.
Line 62, reads "indicator a" and should read -- indicator of a --.

Signed and Sealed this

Twenty-ninth Day of July, 2003

JAMES E. ROGAN
*Director of the United States Patent and Trademark Office*